US 6,235,973 B1

(12) United States Patent
Smith et al.

(10) Patent No.: US 6,235,973 B1
(45) Date of Patent: May 22, 2001

(54) EXPRESSION OF MAGAININ AND PGL CLASSES OF ANTIMICROBIAL PEPTIDE GENES IN PLANTS, AND THEIR USE IN CREATING RESISTANCE TO MULTIPLE PLANT PATHOGENS

(75) Inventors: Franzine Smith, Geneva, NY (US); Alan D. Blowers, St. Charles, IL (US); Joyce Van Eck, Ithaca; John Sanford, Geneva, both of NY (US)

(73) Assignee: Sanford Scientific, Inc., Waterloo, NY (US)

( * ) Notice: Subject to any disclaimer, the term of this patent is extended or adjusted under 35 U.S.C. 154(b) by 0 days.

(21) Appl. No.: 09/127,680

(22) Filed: Jul. 31, 1998

Related U.S. Application Data

(60) Provisional application No. 60/054,315, filed on Jul. 31, 1997.

(51) Int. Cl.[7] .............................. C12N 5/04; C12N 15/82; C12N 15/31; C12N 15/87; A01H 5/00
(52) U.S. Cl. .................... 800/279; 435/69.1; 435/419; 435/468; 800/288; 800/301; 800/323.1
(58) Field of Search ................................ 435/69.1, 320.1, 435/410, 419, 468; 536/24.1; 800/278, 279, 288, 295, 298, 301, 323.1

(56) References Cited

U.S. PATENT DOCUMENTS

| 5,254,537 | 10/1993 | Zasloff .................................. 514/13 |
| 5,424,395 | 6/1995 | Bascomb et al. . | |

FOREIGN PATENT DOCUMENTS

| 0 359 472 | 3/1990 | (EP) | .............................. C12N/15/32 |
| 0 472 987 | 3/1992 | (EP) | ................................ C07K/7/10 |
| 502718A | * 4/1992 | (EP) | .............................. A01N/37/46 |
| 0 502 718 | 9/1992 | (EP) | .............................. A01N/37/46 |
| WO 90/11770 | 10/1990 | (WO) | .............................. A61K/37/02 |
| WO 96/04373 | 2/1996 | (WO) | .............................. C12N/15/10 |

OTHER PUBLICATIONS

Montanelli and Nascari, *J. Genet. & Breed.* 45:307–316 (1991).
Nordeen et al., *Plant Science*, 82 (1992) 101–107.
Hightower et al., *Plant Cell Reports* (1994) 13:295–299.
De Bolle et al., *Plant Molecular Biology* 31:993–1008, 1996.
Destefano Beltran, *The Introduction Into Tobacco Plants of Genes Which Encode Some of the Natural Components of the Humoral Immune Response of Hyalophora Cecropia*, UMI, 300 N. Zeeb Rd., Ann Arbor, MI 48106 (c. 1993).
Qui et al., (1995) *Plant Cell Reports*, vol. 15, No. 1/2 pp. 115–118.
Wilson et al., (1995) *New Zealand Natural Sciences*, vol. 22, pp. 43–50.
Lin et al, Plant Mol. Biol., vol. 23, pp. 489–499, 1993.*
Hancock and Lehrer. *Trends in Biotechnology*. 16:82–88 (1998).
Broekaert et al. *Critical Reviews in Plant Sciences*. 16:297–323 (1997).
Florak et al. *Transgenic Res.* 4:132–141 (1995).
Bevins and Zasloff. *Ann. Rev. Biochem.* 59:395–414 (1990).
Andreu et al. *Eur. J. Biochem.* 149:531–535 (1985).
Maloy and Kari. *Biopolymers.* 37:105–122 (1995).
Broekaert et al. *Plant Physiol.* 108:1353–1358 (1995).
Terras et al. *Plant Cell.* 7:573–588 (1995).
Mendenez et al. *Eur. J. Biochem.* 194:533–539 (1990).
Hightower et al. *Plant Cell Report.* 13:295–299 (1994).
Carmona et al. *Plant J.* 3:457–462 (1993).
Jaynes et al. *Plant Sci.* 89:43–53 (1993).
Melchers et al. *Plant Mol. Biol.* 21:583–593 (1993).
Pang et al. *Gene.* 112:2279–234 (1992).
Odell et al. *Nature.* 313:810–812 (1985).
Kay et al. *Science.* 236:1299–1302 (1987).
Sanford et al. *Methods Enzymol.* 217:483 (1992).
Klien et al. *Nature.* 327:70–73 (1987).
Lee et al. *Nature Biotechnology.* 15:178–182 (1997).

* cited by examiner

*Primary Examiner*—Gary Benzion
*Assistant Examiner*—Ashwin D. Mehta
(74) *Attorney, Agent, or Firm*—McDonnell Boehnen Hulbert & Berghoff

(57) ABSTRACT

The invention provides antimicrobial peptides, nucleic acid constructs encoding them, methods for transforming plant cells, and transgenic plant tissue that expresses the antimicrobial peptide genes and thereby exhibit improved resistance to plant pathogens.

24 Claims, 1 Drawing Sheet

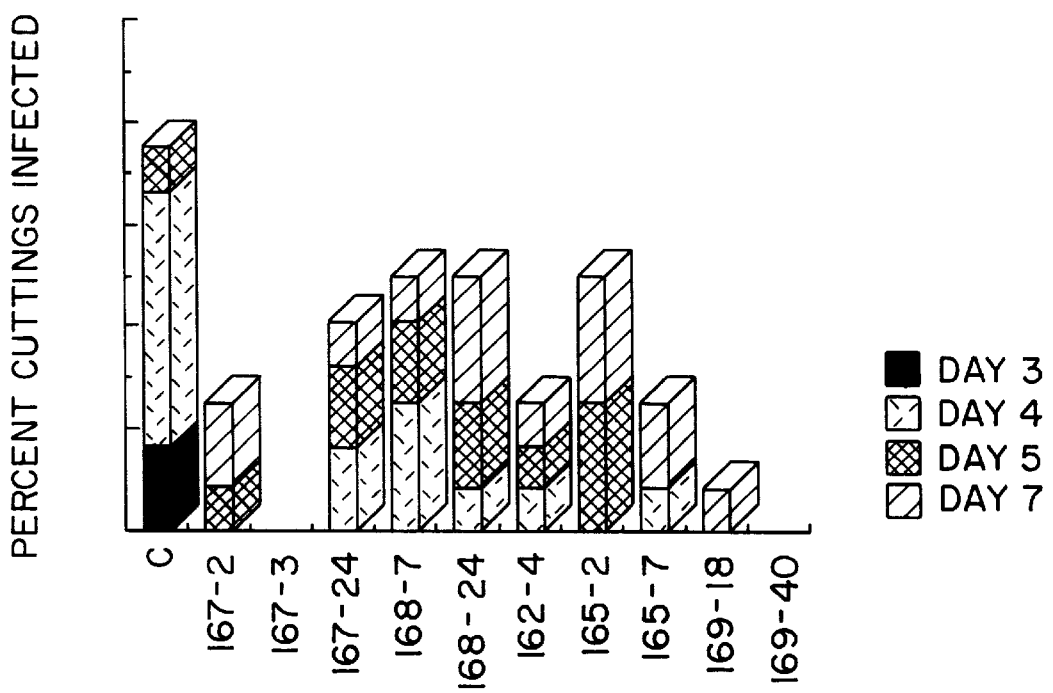

EXPRESSION OF MAGAININ AND PGL CLASSES OF ANTIMICROBIAL PEPTIDE GENES IN PLANTS, AND THEIR USE IN CREATING RESISTANCE TO MULTIPLE PLANT PATHOGENS

This application claims the benefit of U.S. Provisional Application No. 60/054,315, filed Jul. 31, 1997.

BACKGROUND OF THE INVENTION

1. Field of the Invention

The present invention relates to transgenic plants having surprisingly improved resistance to plant pathogens due to expressed antimicrobial peptide genes, particularly Magainin and PGL classes of peptide genes, in the plants.

2. Description of the Related Art

In recent years, it has become widely recognized that many organisms, including plants, utilize peptides as a component of their host defense strategies (for review see Hancock and Lehrer. *Trends In Biotechnology* 16:82–88 (1998) or Broekaert et al., Critical Reviews in Plant Sciences 16:297–323 (1997)). These broad-spectrum antibiotic peptides have been shown to be active against Gram-negative and Gram-positive bacteria, fungi and protozoa. Overexpression of both plant- and non-plant-derived (e.g., amphibian and insect) antimicrobial peptides with antimicrobial activity in transgenic plants has been touted by some as a means to confer pest resistance in crop plants. However, published reports describing transgenic tobacco plants expressing antimicrobial peptides revealed generally disappointing results (Florak et al., *Transgenic Res.* 4:132–141 (1995)). In several cases, the antimicrobial peptides failed to accumulate to significant amounts within the plant cell as rapid degradation of the peptide was observed. For this reason, and also due to serious concerns about potentially phytotoxic effects exerted by the antimicrobial peptides when expressed in plants, plant scientists have not aggressively pursued this technology.

Antimicrobial peptides can be classified into many categories based upon their structure (e.g., linear vs. cyclic), their size (20–45 amino acids) and their source (e.g., insect, amphibian, plant). However, despite their apparent diversity, numerous defense-related peptides have the common features of being highly basic and being capable of forming amphipathic structures. These unifying features suggest that most peptides appear to act by a direct lysis of the pathogenic cell membrane. Their basic structure facilitates their interaction with the cell membrane, and their amphipathic nature allow them to be incorporated into the membrane ultimately disrupting its structure.

Frog skin secretions of the African clawed frog, *Xenopus laevis*, have been discovered to be a particularly rich source of antibiotic peptides (Bevins and Zasloff *Ann. Rev. Biochem.* 59:395–414 (1990)). Known peptides include magainins, PGL$^a$, xenopsin and caerulein. Magainins 1 and 2 are very closely related; each are 23 residues in length, contain no cysteine, and form an amphipathic α helix. PGL$^a$ is a small peptide processed from a larger precursor and is both cationic and amphipathic in nature (Andreu et al., *Eur. J. Biochem.* 149:531–535 (1985)). It has the somewhat unusual feature of containing a COOH-terminal amide group rather than the expected carboxyl group. Moreover, it has been reported that magainin 2 (but not magainin 1) and PGL$^a$ can interact synergistically with one another to exert enhanced levels of antibacterial activity (U.S. Pat. No. 5,254,537). Magainin/PGL peptides co-evolved in the frog, which may explain the synergy. Maloy and Kari, *Biopolymers* 37, 105–122 (1995) describe, inter alia, the magainin and PGL classes of peptides.

Insects have also been demonstrated to possess a variety of defense-related peptides (Boman and Hultmark. *Ann. Rev. Biochem.* 41:103–126 (1987)). Cecropins from moths and flies are slightly larger than the frog-derived peptides (31–39 residues), are basic due to the presence of multiple arginine and lysine residues, and therefore interact strongly with the negatively charged lipid bilayers. Studies of these peptides have shown that they form an N-terminal α-helical region connected by a hinge region to a C-terminal α-helical domain.

Other antimicrobial peptides, termed defensins (for review, see Broekaert et al., *Plant Physiol.* 108:1353–1358 (1995)) have been isolated from radish (Terras et al., *Plant Cell.* 7:573–588 (1995)) and barley (Mendenez et al., *Eur. J. Biochem.* 194:533–539 (1990)), and feature a more complex three-dimensional structure which includes cysteine-stablized triple anti-parallel β sheets with an α-helix. Terras et al., (1995) reported very good levels of protection against infection by Alternaria in transgenic tobacco which overexpressed the radish AFP2 protein. However, a threshold level of AFP2 peptide (which was not easily obtained) in the transgenic plants was required to detect any significant level of disease resistance.

In addition to the naturally-occurring peptides, a wide array of synthetic analogs representing deletion, substitution and variable chain length derivatives have been generated for structure/activity relationship studies. Not unexpectedly, a number of these synthetic variants exhibit increased antimicrobial activity against bacteria and fungi. Moreover, in some cases, not only has the potency of the synthetic antimicrobial peptides to microbes increased dramatically, but their spectrum of antimicrobial activity has also broadened.

Reports of expression of antimicrobial peptides in transgenic plants is rather limited, and the conclusions which have been reached are inconsistent. Montanelli and Nascari, *J. Genetic Breed.* 45:307–316 (1991) introduced the cecropin gene into potato and showed antibacterial activity associated with extracts prepared from fresh tissue, but no demonstration of resistance of the whole plant. Hightower et al., *Plant Cell Report* 13:295–299 (1994). reported similar disappointing results against a bacterial pathogen after introducing the cecropin gene into tobacco. In contrast, Carmona et al., *Plant J.* 3:457–462 (1993) and Jaynes et al., *Plant Sci.* 89:43–53 (1993) observed that transgenic tobacco plants expressing α-thionin and Shiva-1 (a modified cecropin) were more resistant to infection by bacterial pathogens. Clearly, a need exists for transgenic plants having improved resistance to plant pathogens due to expressed antimicrobial peptide genes therein. Specifically, peptides belonging to the magainin and PGL$^a$ classes needed to be tested in this regard.

SUMMARY OF THE INVENTION

The present invention provides antimicrobial peptides, particularly Magainin and PGL classes of peptides, and the genes and other nucleic acid constructs that encode for the peptides. In particular, the peptides according to the invention are effective against phytopathogenic microbes including bacteria, fungi, and phytoplasma. The invention also provides methods of conferring antimicrobial resistance on plant tissue plants by transforming the plant tissue with a nucleic acid construct encoding such peptides. Further provided by the invention are transgenic plant tissues that are resistant to a broad range of microbes. Essentially any plant transformed to express one or more of the antimicrobial peptides according to the invention will manifest resistance to a broad range of microbes, particularly bacteria and fungi.

Prior to the invention, it was uncertain whether the Magainin and PGL classes of antimicrobial peptides would confer resistance in plants to fungal pathogens as well as bacterial pathogens. As shown herein, this class of peptides does have impressive anti-fungal properties. An important advantage provided by the invention results from the fact that Magainin and PGL classes of peptides are derived from frogs and are known to have low vertebrate and mammalian toxicity, and Magainin class peptides have a history of pharmaceutical use.

The representative, non-limiting, discoveries of the present invention include:

1) antimicrobial peptides that possess potent anti-phytopathogenic fungal activity (particularly the Magainin and PGL classes of peptides Magainin 2, MSI-99, MSI-55, and PGL, but also D5-C) in addition to anti-phytopathogenic bacterial activity;
2) antimicrobial peptides that are particularly effective against specific pathogens (e.g., MSI-99 and D5-C are especially active against the fungus, Phytophthora);
3) synthetic genes encoding antimicrobial peptides and, in particular, Magainin and PGL classes of peptides, which can be fused to strong promoters (e.g. E35S, UBQ3, and UBQ10), and lead to high levels of peptide accumulation in transgenic plants;
4) the UBQ3 promoter which expresses transgene products very highly in flower petal tissues;
5) the pea vicilin signal peptide sequence, which effectively targets antimicrobial peptides out of the cell and into the extracellular space;
6) transgenic plants that express high levels of the antimicrobial peptide (particularly Magainin and PGL classes of peptides) and that exhibit significant levels of resistance to a broad range of phytopathogens including both fungi and bacteria; bacteria as diverse as Erwinia, Pseudomonas, and Xanthomonas, and fungi as diverse as Botrytis, Phytophthora, and powdery mildew;
7) the peptides of the present invention behave very similarly in all transgenic plant species examined to date (e.g., petunia, geranium, poinsettia, and lisianthus)—and confer similar broad-spectrum resistance;
8) the present peptides that, when expressed at high levels, confer resistance to infection by phytoplasma—a class of resistance never achieved previously.
9) the present peptides can be used in combination to achieve stronger and broader levels of resistance;
10) two specific peptides, magainin 2 and PGL, act synergistically against a wide range of plant pathogens in vitro and when co-expressed in planta also manifest a synergy against the plant pathogens (particularly fungi), thereby enhancing disease resistance levels;
11) this synergy allows recovery of transgenic plants containing less total amount of peptide, yet with the same or greater level of disease resistance, thus enabling screening of fewer transgenic plants co-expressing these two peptides to identify resistant lines (when compared to those plants expressing a single antimicrobial peptide only);
12) a method to maximally utilize the synergy described above by expressing each peptide at sub-phytotoxic levels in different cellular compartments (e.g., one peptide localized in the cytosol and the other expressed either extracellularly or in the plant plastid)—if during pathogen attack, the cell membranes lose their integrity, the compartmentalized peptides are then free to interact (synergistically) and kill the invading pathogen;
13) the present peptides can be used to target other plant pests, such as nematodes and viruses;
14) the present antimicrobial-peptide genes can be expressed in the plant plastid, or the peptides can be transported there by use of signal peptides;
15) antimicrobial peptide-expressing genes can be used in concert with other disease resistance genes to achieve stronger, broader, and more durable resistance;
16) A "window of expression" can be achieved within plants wherein antimicrobial peptide activities are high enough for control of pathogens, but still low enough to have no adverse effect on the plant.

The foregoing merely summarizes certain aspects of the invention and is not intended, nor should it be construed, as limiting the invention in any manner. All patents, patent applications, and other publications recited herein are hereby incorporated by reference in their entirety.

BRIEF DESCRIPTION OF THE DRAWING

The figure graphically illustrates incidence of *Erwinia carotovova* ss *carotovora* infection of inoculated poinsettia cuttings.

DETAILED DESCRIPTION OF THE PREFERRED EMBODIMENTS

In a first aspect, the present invention provides a series of superior antimicrobial peptides (also known as "lytic" peptides) that are active against both plant pathogenic fungi and plant pathogenic bacteria. Preferred antimicrobial peptides according to the invention are those of the Magainin and PGL classes of of peptides. These peptides are especially active in vitro. The present inventors demonstrate herein that levels of peptides are achieved in transgenic plant tissue that are effective in disease control with no obvious phytotoxic effects to the host plant tissue. The peptides accumulate to high levels either in the cytosol or the intercellular space when expressed in a variety of plants. The peptides according to the invention confer on plants increased resistance to infection against a broad-spectrum of phytopathogens including both fungi as diverse as Botrytis, Phytophthora, and powdery mildew and bacteria as diverse as Erwinia, Pseudomonas, and Xanthomonas as well as against phytoplasma—a class of resistance never achieved previously.

The Magainin and PGL classes of peptides according to the instant invention were derived from magainin and PGL$^a$ peptides provided by Magainin Pharmaceuticals, Inc. (magainins and PGL$^a$). These were evaluated for antimicrobial activity against a wide range of bacterial and fungal phytopathogens. The primary amino acid sequences of the peptides are given in the Sequence Listing. We compared the Magainin and PGL classes of antimicrobial peptides against one cecropin class peptide derived from a peptide provided by Demeter BioTechnologies.

The in vivo expressed magainin/PGL type peptides of this invention differ from the peptides found in nature. They differ from their natural counterparts by, inter alia, having an N-terminal Met residue. In addition, PGL contains the characteristic —COOH group at its C-terminus resulting from in vivo synthesis whereas the naturally occurring PGL$^a$ has a C-terminal amide resulting from processing from a precursor protein. Although these differences may appear at first glance to be relatively small, because the magainin peptide itself is small, such small alterations can have profound affects on the peptide's properties. Consequently, one could not have reasonably predicted what affects, if any, such changes (which result in a change in charge of the peptide) would have on the peptide's antimicrobial properties.

MSI-99 and MSI-55 are substitution derivatives of magainin 2 and PGL, respectively. Among the amino acid differences between magainin 2 and MSI-99 are the substitution in MSI-99 of Lys for His at position 8 (using the numbering given in the Sequence Listing) and Lys for Gly at position 19, and in place of the Met at position 22 in magainin 2 is a Leu residue in MSI-99. Although the primary amino acid sequences of PGL and MSI-55 differ significantly, the amphipathic α helical structure that they assume is very similar. The peptides were chemically synthesized and purified to homogeneity.

D5-C is a synthetic derivative of cecropin B. As demonstrated herein, the D5-C peptide, with an N-terminal methionine added, is an exceptionally effective cecropin peptide for use in engineering plant disease resistance. This is the best cecropin class peptide of which we are aware.

Significantly, we show that magainin class peptides are equal or better for enhancing plant disease resistance. The magainin 2 peptide (with a methionine added at the N-terminus) is equally efficacious as D5-C, and MSI-99 is for many organisms better. Likewise, we show that PGL class peptides with N-terminal addition of methionine and without the C-terminal arnide group are especially efficacious (i.e., MSI-55). Lastly, we have shown that the previously known in vitro synergy of magainin 2 and PGL is highly effective in planta, even with the addition of N-terminal methionines and without the C-terminal amide group. This powerful synergy can clearly be exploited to achieved higher levels of disease resistance.

The invention according to this first aspect provides both peptides that are designed to be localized in the cytosol as well as those designed to be secreted and localized in extracellular space of plant tissues. In a preferred embodiment, the peptides according to the invention are Magainin and PGL classes of peptides, as represented and exemplified by magainin 2 ("Mag 2"), PGL, MSI-55, and MSI-99. Preferred cytosol-localized peptides are SEQ ID NOs: 2, 6, 10, and 14. Extracellular localized peptides (denoted by appending "*S" to the name of the cytosol localized counterpart, e.g., MSI-99*S) according to the invention further comprise a signal peptide to facilitate secretion of the antimicrobial peptide from the cell. A preferred signal peptide is the pea vicilin signal peptide. Preferred extracellular localized peptides are SEQ ID NOs: 4, 8, 12, 16 and 18.

As described and demonstrated herein, the peptides according to this aspect of the invention are antimicrobial in nature. They are useful for conferring microbe resistance on plant tissue that express the peptides. As used herein, for simplicity "plant tissue" refers to individual plant cells and multicellular plant tissue, including whole plants. Aside from this in vivo utility, the peptides are also useful in vitro as research tools for studying the biological processes involved in microbe infection of plants cells.

Peptides according to the invention can be synthesized in any convenient manner using art recognized techniques, including solid phase synthesis as well as (and preferably) expression by transgenic cells (e.g., plant cells) that have been transformed with a nucleic acid construct encoding the peptides. Examples of transgenic expression are given below. Purification of the peptides, if so desired, can also be accomplished by art recognized techniques.

In a second aspect, the invention provides genes and other nucleic acid constructs encoding for and capable of expressing the peptides according to the invention. The general rules that were followed for construction of the peptide's genes included: (i) incorporation of the consensus sequence for translation initiation around the initiator codon to allow for optimal translation efficiency of the transcript; (ii) utilization of preferred dicot plant codons; and (iii) avoidance of long stretches of A and T residues which can destabilize RNA transcripts or inadvertently signal for polyA addition or intron splicing events. Accordingly, SEQ ID NOs: 1, 5, 9, and 13 are preferred for expressing cytosol localized peptides and SEQ ID NOs: 3, 7, 11, 15, and 17 are preferred for expressing extracellular localized peptides. If a signal peptide other than the pea vicilin signal peptide is desired, the appropriate coding sequence can be appended to one of SEQ ID NOs: 1, 5, 9, or 13 to yield a construct capable of expressing an extracellular localized antimicrobial peptide. In general, however, any nucleic acid derived from any of the foregoing nucleic acid sequences by one or more degenerate nucleotide substitutions will be capable of expressing the active antimicrobial peptide in vivo as long as at least 70% homology to the parent nucleic acid is maintained. The invention also encompasses such genes.

The nucleic acid constructs according to this aspect of the invention are those that when inserted into a plant cell nucleus express a peptide according to the first aspect of the invention. Expression of such nucleic acid constructs can be accomplished after recombination into the plant cell nuclear genome or from a construct (e.g., a plasmid) containing the coding sequence that has not recombined into the nuclear genome.

As demonstrated hereinbelow, the antifungal effect of the combination of magainin 2 and PGL is surprisingly synergistic. Accordingly, in another preferred embodiment of this aspect of the invention, a nucleic acid construct is provided that encodes both the magainin 2 and PGL peptides, both independently with or without a signal peptide (preferrably the pea vicilin signal peptide) for facilitating extracellular secretion. This embodiment advantageously enables expression of effective amounts of each peptide that would, in the absence of the other peptide, be insufficient to confer microbial resistance.

In preferred embodiments, the nucleic acid constructs, in addition to one of the foregoing coding sequences, further comprise one or more control elements. Preferred among the control elements are plant promoters. Any plant promoter can be used. Preferred plant promoters include the E35S, UBQ3, UBQ10, UBQ11, and UBQ14 promoters.

The nucleic acids according to this aspect of the invention can be made by art recognized techniques, as exemplified in the Examples below. As described and demonstrated herein, the nucleic acids according to this aspect of the invention are useful for expressing the antimicrobial peptides according to the first aspect of the invention.

In a third aspect, the invention provides a method of conferring resistance to plant tissue against a variety of microbes, including, but not limited to, fungi, bacteria, and phytoplasmas. The method comprises transforming a plant tissue with a nucleic acid construct according to the second aspect of the invention, which transformed tissue is thereby enabled to express one or more antimicrobial peptides according to the first aspect of the invention at levels sufficient to confer microbial resistance to the cell. The method according to this aspect of the invention advantageously allows for levels of expression sufficient to provide resistance to phytopathogenic microbes without otherwise affecting the plant cells.

In a preferred embodiment, the method comprises transforming plant tissues with one or more nucleic acid constructs that result in the plant tissues expressing two or more antimicrobial peptides according to the invention. The two peptides are preferably separately compartmentalized (i.e., one peptide is in one of the plastid, cytosol, or extracellular space and the other peptide is in another of the plastid, cytosol, or extracellular space).

In a more preferred embodiment, the method comprises transforming plant tissue with one or more nucleic acids to cause the tissue to express both the magainin 2 and PGL peptides, both independently with or without a signal peptide (preferably the pea vicilin peptide) for facilitating extracellular secretion. The magainin 2 and PGL peptides in this embodiment can be in the same compartment or in separate compartments.

Transformation can be accomplished by any art recognized technique for transforming plant cells. In a preferred embodiment, transformation is accomplished via the biolistic method. Selection of transformed plant tissues can be accomplished by art recognized techniques, such as through co-transformation with a selectable marker gene.

Transformation can be accomplished in either the nucleus or the plastid, as determined by the targeting regions of the nucleic acid construct. Details of plastid transformation can be found, e.g., in co-pending international application PCT/US98/15289 (WO 99/05265), entitled, "Improved Plastid Transformation Of Higher Plants And Production Of Transgenic Plants With Herbicide Resistance," filed Jul. 23, 1998, and U.S. application Ser. No. 08/899,061, filed Jul. 23, 1997, now abandoned.

In a fourth aspect, the invention provides microbe resistant transgenic plant tissue that is transformed with and expresses a gene or genes encoding one or more antimicrobial peptides, particularly Magainin and PGL classes of peptides. The transgenic plant tissue is made according to the third aspect of the invention. Whole transgenic plants can be obtained by growing transgenic plant cells or tissue according to art recognized techniques.

The present invention is further described and illustrated by the following examples that are provided solely for purposes of illustration and are not intended, nor should they be construed, as limiting in any manner. Those skilled in the art will appreciate that variations and modifications of the following Examples can be made without exceeding the spirit or scope of the invention.

EXAMPLES

Example 1

In Vitro Sensitivity of Phytopathogens to Magainin and PGL Classes of Antimicrobial Peptides Known amounts of pathogen were added to serial dilutions of peptide ranging from 0 up to 256 µg/ml in individual wells of a 96-well microtiter plate. An equivalent volume of growth medium (Luria Bertani (LB) broth for bacteria and potato dextrose broth (PDB) for fungi) was added to each well and the plates incubated overnight at 25° C. with gentle shaking. The following day, wells were scored for the presence or absence of growth; the lowest concentration of peptide which inhibited all growth was recorded as the minimum inhibitory concentration (MIC) value. The phytopathogenic bacteria employed in the assays included *Pseudomonas syringae* and *Erwinia carotovora*. The phytopathogenic fungi included two isolates of *Phytophthora parasitica* (from petunia and vinca), *Fusarium solani*, *Fusarium graminearum*, *Thielaviopsis basicola*, *Botrytis cinerea* and *Rhizoctonia solani*.

As can be observed in Table 1, the bacteria were extremely sensitive (MIC<2 µg/ml) to the action of the antimicrobial peptide analogs, MSI-99 and D5-C. By contrast, the natural peptides, magainin 2 and PGL alone were significantly less active against log phase-grown Pseudomomas and Erwinia. However, when combined in equimolar amounts, the magainin 2/PGL combination was even more potent than the peptide derivatives (MIC=0.5 µg/ml).

In regards to the fungi, conidiospores of *Fusarium solani*, *Fusarium graminearum*, *Thielaviopsis basicola*, and *Botrytis cinerea* were collected from potato dextrose agar (PDA) plates by flooding a two week-old culture with a solution of 0.01% Tween 20 and rubbing the surface. The resultant spore suspension was filtered through glass wool to remove mycelial fragments. The spore concentration was then determined with a haemocytometer. When pregerminated spores were utilized, spore suspensions were prepared several hours prior to use (when the length of the germ tube equaled that of the spore). For *Rhizoctonia solani*, mycelial fragments were used instead of spores. A two week-old PDB culture of Rhizoctonia was chopped in a blender to produce mycelial fragments that were approximately four cells long. A haemocytometer was then used to determine the concentration of fragments. For *Phytophthora parasitica*, zoospores raised in liquid culture were used for the assay.

Each of the fungi assayed were sensitive to the action of at least one of the single antimicrobial peptides (Table 1). For example, both Fusarium species were extremely sensitive to treatment with the four single antimicrobial peptides. In contrast, the two Phytophthora isolates were relatively resistant to the natural antimicrobial peptides, with peptide analogs MSI-99 and D5-C showing the best anti-Phytophthora activity. *Thielaviopsis basicola, Botrytis cinerea* and *Rhizoctonia solani* exhibited intermediate levels of sensitivity to the various single peptides. Antimicrobial peptide treatment of germinated and non-germinated spores produced essentially identical results. MSI-55 also displayed potent anti-bacterial and anti-fungal activity in vitro.

TABLE 1

| | Minimum Inhibitory Concentration[a] (µg/ml) | | | | |
| --- | --- | --- | --- | --- | --- |
| Phytopathogen | Mag 2 | PGL | MSI-99 | D5-C | Mag 2/ PGL[b] |
| *Pseudomonas syringae* | 32 | >64 | 1 | NA[c] | 2 |
| *Erwinia carotovora* | 32 | 32 | 1 | 2 | 0.5 |
| *Phytophthora parasitica* (vinca) | | | | | |
| non-germinated | >256 | >256 | 64 | 16 | >32 |
| germinated | >128 | >128 | 16–32 | 16–32 | >64 |

TABLE 1-continued

| Phytopathogen | Minimum Inhibitory Concentration[a] (μg/ml) | | | | |
|---|---|---|---|---|---|
| | Mag 2 | PGL | MSI-99 | D5-C | Mag 2/ PGL[b] |
| *Phytophthora parasitica* (petunia) | | | | | |
| non-germinated | NA | NA | NA | NA | NA |
| germinated | >128 | >128 | 8–16 | 16–32 | >64 |
| *Fusarium solani* | | | | | |
| non-germinated | 4 | 4 | 2 | 4 | 2 |
| germinated | 4–8 | 8–16 | 4 | 4 | 2 |
| *Fusarium graminearum* | | | | | |
| non-germinated | 4– | 4–8 | 4 | NA | 2 |
| germinated | NA | NA | NA | NA | NA |
| *Thielaviopsis basicola* | | | | | |
| non-germinated | 8 | 4–8 | 4 | 16 | 4 |
| germinated | 4 | 4 | 4 | 16 | 2 |
| *Botrytis cinerea* | | | | | |
| non-germinated | 8–16 | 4–8 | 8 | NA3 | 1–2 |
| germinated | 8 | 8 | 8 | NA | 1–2 |
| *Rhizoctonia solani* R2 | | | | | |
| mycelial fragments | 16–32 | 16–32 | 16 | 32–64 | 2–4 |

[a]MIC: minimum peptide concentration required to inhibit all microbial growth after 24 hrs.
[b]equimolar amounts of peptide added
[c]not assayed Overall, the most potent antimicrobial peptide treatment was the magainin 2/PGL combination; all the fungi were extremely sensitive to this combination with the exception of Phytophthora. For example, the MIC value for *Rhizoctonia solani* with the combination was 2–4 μg/ml, nearly an order of magnitude less than the 16–32 μg/ml required with magainin 2 or PGL alone. A similar, though less dramatic difference was also observed with Phytophthora, Botrytis and Fusarium. Taken together, these results clearly demonstrate that broad spectrum anti-microbial activity was exhibited collectively by this group of antimicrobial peptides. Consequently, one would expect that essentially all phytopathogenic fungi and bacteria will manifest sensitivity to Magainin and PGL classes of peptides.

Example 2

Construction of Antimicrobial Peptide Genes

The general strategy to assemble these small genes was to chemically synthesize two partially overlapping single-strand oligonucleotides, allow the homologous regions to hybridize, and then complete the double strands in both directions by extension with Taq DNA polymerase. The oligonucleotide pair for each gene was designed with unique restriction sites located on each end of the gene (Bam HI and Sst I at the 5' and 3' ends, respectively) to allow directional cloning into plant expression vectors after restriction digestion. The general rules that were followed for gene construction included: (i) incorporation of the consensus sequence for translation initiation around the initiator codon to allow for optimal translation efficiency of the transcript; (ii) utilization of preferred dicot plant codons; and (iii) avoidance of long stretches of A and T residues which can destabilize RNA transcripts or inadvertently signal for polyA addition or intron splicing events. All clones were subjected to DNA sequence analysis to verify authenticity of the expected gene sequence. The nucleotide sequences of these antimicrobial peptide genes and the corresponding peptide sequences are displayed in the Sequence Listing, infra, as SEQ ID NOs: 1, 2, 5, 6, 9, 10, 13, and 14.

Previous crop protection studies utilizing transgenes have demonstrated that disease resistance levels can be influenced by the cellular location of the defense protein. For example, Melchers et al., *Plant Mol. Biol.* 21:583–593 (1993) demonstrated that optimal levels of resistance against infection by Fusarium were achieved by secretion of chitinase and β-1,3-glucanase into the intercellular space of transgenic tomato plants. These results are hardly surprising since PR-proteins (or pathogenesis-related proteins, of which chitinase and glucanase are members), induced after pathogenic attack, can be found in numerous cellular compartments, including the cytosol and the vacuole, as well as extracellularly.

The antimicrobial peptide genes first constructed as described above were designed to be translated and accumulate within the cytosol. It is possible that better protection against invading pathogens may be afforded, however, by secretion of the antimicrobial peptides into the intercellular space of the plant. To transport the antimicrobial peptides out of the plant cell, the signal peptide for the pea vicilin protein was fused in-frame (translationally) to the N-terminus of the antimicrobial peptides. Previously, the 15-amino acid signal peptide of the pea vicilin protein had been demonstrated to direct efficient secretion of β-glucuronidase into the intercellular space of whole transgenic tobacco plants or into the liquid medium from transformed tobacco NTI suspension cells (Pang et al., *Gene*. 112:229–234 (1992). The vicilin signal peptide was very efficient in directing protein transport as little β-glucuronidase accumulated in the cytoplasm or remained sequestered in the endoplasmic reticulum. It was hypothesized that a protein secretion default pathway was the route of extracellular transport for the modified GUS enzyme.

An oligonucleotide that encoded the pea vicilin signal peptide was employed in PCR's to create antimicrobial peptides that are directed to the intercellular space. The nucleotide sequences of the antimicrobial peptide genes and the corresponding peptides designed for secretion are presented in the Sequence Listing as SEQ ID NOs: 3, 4, 7, 8, 11, 12, 15, 16, 17, and 18. Since the signal peptide is cleaved during the secretory process, the final structure of the mature antimicrobial peptides are essentially no different than those peptides which lack this modification.

The completed antimicrobial peptide genes were then placed under the transcriptional control of one of four promoters. The well-characterized native and enhanced versions of the CaMV 35S promoter were utilized (Odell et al., *Nature*. 313:810–812 (1985) and Kay et al., *Science* 236:1299–1302 (1987)). Also, the promoters of the UBQ3 and UBQ10 genes, members of the polyubiquitin gene family in *Arabidopsis thaliana*, were employed (Norris et al., *Plant Mol. Biol.* 21:8995–8906 (1993)). We have observed that the UBQ3 and UBQ10 promoters direct high levels of gene expression in transgenic petunia. All antimicrobial peptide genes were flanked at their 3' ends by the nos 3' sequence containing the signal for polyA addition to the transcript. Tables 2 and 3 lists some of the relevant antimicrobial peptide expression cassettes which have been created for introduction into various species. All antimicrobial peptide expression cassettes were constructed in pUC-derived cloning vectors.

TABLE 2

Plasmids for cytosolic localization of antimicrobial peptides

| Antimicrobial peptide | Promoter | | | |
|---|---|---|---|---|
| | 35S | E35S | UBQ3 | UBQ10 |
| Magainin 2 | NA[a] | pSAN142 | pSAN163 | pSAN283 |
| PGL | NA | NA | NA | NA |
| MSI-55 | pSAN162 | pSAN141 | NA | NA |
| MSI-99 | NA | pSAN143 | pSAN164 | pSAN284 |
| D5-C | NA | pSAN144 | pSAN165 | NA |

[a]Not applicable

TABLE 3

Plasmids for extracellular localization of antimicrobial peptides

| Antimicrobial peptide | Promoter | | |
|---|---|---|---|
| | E35S | UBQ3 | UBQ10 |
| Magainin 2 | pSAN146 | pSAN167 | pSAN284 |
| PGL | pSAN313 | pSAN315 | pSAN316 |
| MSI-55 | pSAN145 | pSAN166 | NA[a] |
| MSI-99 | pSAN147 | pSAN168 | pSAN285 |
| D5-C | pSAN158 | pSAN169 | pSAN354 |
| Mag 2/PGL | NA | pSAN318-321 | pSAN318-321 |

[a]Not applicable

For construction of a vector that would express both magainin 2 and PGL, a total of four plasmids were assembled. To construct plasmids pSAN318 and pSAN319, the UBQ3::magainin 2 and UBQ10::PGL cassettes were combined onto a single plasmid in two orientations (the opposite and same directions of transcription for pSAN318 and pSAN319, respectively). Similarly, the UBQ3::PGL and UBQ10::magainin 2 cassettes were situated on a single plasmid in two orientations (the opposite and same directions of transcription for pSAN320 and pSAN321, respectively) to generate plasmids pSAN320 and pSAN321.

Example 3

Plant Cell Transformation

All transformations reported herein employed the biolistic technique (for review, see Sanford et al., *Methods Enzymol.* 217, 483 (1992)), comprising bombarding the cells to be transformed with DNA-coated microparticles and the parameters for which are described below.

Petunia

Leaves were harvested from V26 or '1627' plants maintained in vitro on a Murashige and Skoog based medium (MS3S). Shoot tip and nodal cuttings were taken every month and placed on fresh MS3S. Young to middle-aged leaves were harvested from 5 to 6-week-old plants. The leaves were harvested the day of particle bombardment (Klein et al., *Nature* 327:70–73 (1987)) and placed in 100×15 mm Petri dishes containing approximately 25 ml of a petunia regeneration medium obtained from Ball FloraPlant (BFP) (West Chicago, Ill.). They were oriented with the adaxial surface facing upwards. One leaf was placed in the center of the plate, then eight leaves were arranged around this leaf. After bombardment, the leaves were flipped, so that the adaxial surface was now in contact with the medium. Five days after bombardment, the leaves were cut into approximately 0.5 cm$^2$ sections and transferred to regeneration medium containing 100 mg/l kanamycin for V26 or 4 mg/hygromycin plus 250 mg/l carbenicillin for '1627'.

When regenerants were approximately 0.5 cm tall, they were excised from the explants and transferred to MS3S for rooting. They were subcultured once a month by culturing shoot tips on MS3S medium. All cultures were maintained at 25° C. under lights for a 16 hr light period.

Poinsettia

Hypocotyl sections from the cultivars Angelika and Freedom were cultured on a callus induction medium. After 4 weeks, the callus was removed and transferred to an embryo induction medium. At this point, the callus was bombarded. One week after bombardment, the calli were transferred to the embryo induction medium containing 10 mg/l hygromycin. After two weeks, the calli were transferred off selection and onto a developmental medium. The calli remained on this medium for two weeks and were then transferred to a maturation medium where they remained for six weeks. At that time, somatic embryos were selected and transferred to germination medium. Approximately 2 weeks after germination, the small plantlets were transferred to MS3S medium. All cultures were maintained at 25° C. under lights for a 16 hr light period. U.S. application Ser. No. 08/903,944, filed Jul. 31, 1997 (pending), describes the media employed.

Geranium

Stock plants from the geranium Designer Scarlet were maintained in vitro on MS3S supplemented with 1 mg/l IAA. Petiole sections were harvested and cultured on a callus induction medium. After 4 weeks, the callus was placed into geranium suspension medium and maintained on a rotary shaker. The suspensions were subcultured every few weeks. After several months, approximately 1.5 ml of suspension were dispensed onto sterile filter paper which was then transferred to geranium suspension regeneration (GSR) medium provided by BFP (West Chicago, Ill.). The cultures were bombarded 3 days after plating. Two days after bombardment, the cultures were transferred to GSR medium containing 10 mg/l hygromycin. After one month on selection, the cultures were transferred off selection.

Four to 6 weeks after bombardment, small, putatively transformed calli developed and were transferred to GSR when they were approximately 3 mm in diameter. When small, green organized structures formed, they were transferred to GSR medium containing 0.05 mg/l TDZ medium. When the structures became more organized they were transferred to modified GSR medium that had 0.01 mg/TDZ, but no NAA. When they were more shoot-like they were transferred to Intermediate Medium provided by BFP where they remained for 1 to 2 weeks, and then were transferred to Meristem C medium provided by BFP where they remained for 1 to 2 weeks. Small shoots were then transferred to MS3S containing 1 mg/l IAA and were transferred off this medium after 1 week, to MS3S. All cultures were maintained at 25° C. under lights for a 16 hr light period.

Lisianthus

In vitro stock plants of selected inbred cultures were maintained on a rooting medium containing 2 mg/l IAA. The day of bombardment, young to middle-aged leaves were harvested from 1-month-old plants. They were placed in 100×15 mm Petri dishes containing approximately 25 ml of Lisianthus Regeneration medium and oriented with the adaxial surface facing upwards. One leaf was placed in the center of the plate, then eight leaves were arranged around this leaf. After bombardment, the leaves were flipped, so that the adaxial surface was now in contact with the medium. Five days after bombardment, the leaves were cut into approximately 0.5 cm$^2$ sections and transferred to Lisianthus Regeneration medium containing 10 mg/l hygromycin. All cultures were maintained at 25° C. under lights for a 16 hr light period.

Bombardment parameters: Plasmids harboring the antimicrobial peptide expression cassettes were co-bombarded with plasmid DNA containing a plant selectable marker cassette into plant tissues. For all bombardments, M10 tungsten particles were used. For V26 petunia, leaves were bombarded once or twice at a pressure of 1200 psi and a plate distance set at level 6 (12 cm). For '1627', leaves were bombarded once at a pressure of 1200 psi and a plate distance of 12 cm. Each plate was bombarded with 20 ng of DNA (10 ng of the plasmid containing the antimicrobial peptide gene and 10 ng of the plasmid containing the selectable marker gene).

Poinsettia callus was bombarded once at a pressure of 1200 psi and a plate distance set at level 5 (9 cm). Each plate was bombarded with 100 ng of DNA (50 ng of the plasmid containing the antimicrobial peptide gene and 50 ng of the plasmid containing the selectable marker gene).

Geranium suspension cultures were bombarded once at a pressure of 1000 psi and a plate distance set at level 6 (12 cm). Each plate was bombarded with 20 ng of DNA (10 ng of the plasmid containing the antimicrobial peptide gene and 10 ng of the plasmid containing the selectable marker gene).

Lisianthus leaves were bombarded once or twice at a pressure of 1200 psi and a plate distance set at level 6 (12 cm). Each plate was bombarded with 20 ng of DNA (10 ng of the plasmid containing the antimicrobial peptide gene and 10 ng of the plasmid containing the selectable marker gene).

Example 4

Magainin and PGL Classes of Antimicrobial Peptide Expression in Transgenic Plants Anti-Bacterial Bioassays: An efficient and reliable in vitro anti-bacterial bioassay for detection of antimicrobial peptide activity in transgenic plants was developed. Thus far, the present inventors have utilized this bioassay to detect antimicrobial peptide activity in the transgenic plants of four ornamental species, petunia, poinsettia, geranium and lisianthus. Briefly, cell-free extracts were prepared in 25 mM $KPO_4$, pH 5.5 buffer (with the exception of geranium which uses 50 mM $KPO_4$, pH 6.5 buffer supplemented with 0.1% PVP-10) from tissue culture-maintained leaf tissue. Next, $10^3$–$10^4$ Pseudomonas syringae (for poinsettia and geranium) or Pseudomonas cichorni (for petunia and lisianthus) bacteria in LB broth (5 µl) were added to 100 µg of leaf protein in a total volume of 50 µl. After 2–2.5 hrs. incubation at room temperature to allow the peptides to interact with the bacteria, 1 ml LB broth was added to the proteinibacteria mixture and incubated overnight at 28° C. The following day, the tubes were scored for bacterial growth; absence of growth indicates that the bacterial cells were killed by the action of the antimicrobial peptides. An extract prepared from an untransformed plant and the same extract spiked with known amounts of purified antimicrobial peptide were included as negative and positive controls, respectively, in all experiments. Typically, each transformant was subjected to this bioassay four times (two extracts prepared on separate days were assayed in duplicate on each day). Those transgenic lines which exhibited antimicrobial peptide mediated, anti-bacterial activity in 3 out of 4 bioassays were selected for advanced testing. In some cases, we have used immunodetection methods to confirm the amount of antimicrobial peptide in the plant which had been measured by the bioassay. A very useful feature of the assay is that the sensitivity of detection can be adjusted by manipulating the number of bacteria added to the tube. As can be observed in Table 4, typically, 20–50% of the Magainin and PGL classes of peptides transgenic lines subjected to the bioassay tested positive for antimicrobial peptide activity. The actual percentage is highly dependent upon both the class of antimicrobial peptide being expressed and the antimicrobial peptide expression cassette (i.e., promoter considerations).

TABLE 4

Transgenic plants screened for antimicrobial Peptide-mediated Anti-Bacterial/Anti-Fungal Activity

| Crop | Plasmid | Number Recovered and tested | Number Advanced in Anti-Bacterial | Botrytis Leaf Disk Assay | |
|---|---|---|---|---|---|
| | | | | Tested | Advanced |
| Petunia V26 | pSAN141 | 25 | 7 | 7 | 2 |
| | pSAN142 | 21 | 4 | 4 | 1 |
| | pSAN143 | 26 | 6 | 6 | 4 |
| | pSAN144 | 23 | 4 | 4 | 3 |
| | pSAN145 | 16 | 12 | 12 | 6 |
| | pSAN146 | 15 | 3 | 3 | 3 |
| | pSAN147 | 19 | 6 | 6 | 3 |
| | pSAN148 | 9 | 4 | 4 | 2 |
| | pSAN163 | 13 | 4 | 4 | 4 |
| | pSAN164 | 8 | 3 | 3 | 1 |
| | pSAN165 | 12 | 3 | 3 | 1 |
| | pSAN166 | 8 | 4 | 4 | 3 |
| | pSAN167 | 5 | 3 | 3 | 0 |
| | pSAN168 | 2 | 0 | 0 | |
| | pSAN169 | 2 | 0 | 0 | |
| Petunia '1627' | pSAN319 | 9 | 5 | 5 | 2 |
| | pSAN321 | 32 | 16 | 6 | 4 |
| Poinsettia 'Angelika' | pSAN141 | 28 | 6 | 6 | 2 |
| | pSAN142 | 40 | 7 | 7 | 3 |
| | pSAN143 | 19 | 6 | 6 | 3 |
| | pSAN144 | 43 | 5 | 5 | 2 |
| | pSAN145 | 16 | 5 | 5 | 0 |
| | pSAN146 | 15 | 6 | 6 | 3 |
| | pSAN148 | 16 | 5 | 5 | 1 |

TABLE 4-continued

Transgenic plants screened for antimicrobial Peptide-mediated Anti-Bacterial/Anti-Fungal Activity

| Crop | Plasmid | Number Recovered and tested | Number Advanced in Anti-Bacterial | Botrytis Leaf Disk Assay Tested | Advanced |
|---|---|---|---|---|---|
| | pSAN162 | 8 | 3 | 3 | 1 |
| | pSAN163 | 12 | 4 | 3 | 3 |
| | pSAN164 | 3 | 0 | 1 | 0 |
| | pSAN165 | 22 | 7 | 7 | 3 |
| | pSAN166 | 2 | 0 | 0 | 0 |
| | pSAN167 | 24 | 9 | 9 | 2 |
| | pSAN168 | 32 | 9 | 9 | 6 |
| | pSAN169 | 42 | 11 | 1 | 3 |
| | pSAN318 | 3 | 2 | 2 | 2 |
| | pSAN319 | 8 | 8 | 8 | 5 |
| | pSAN320 | 31 | 19 | 10 | 3 |
| Poinsettia 'Freedom' | pSAN168 | 114 | 41 | 41 | 29 |
| | pSAN319 | 90 | 52 | 33 | 17 |
| | pSAN321 | 84 | 49 | 49 | 33 |
| Lisianthus '13450A-6' | pSAN165 | 16 | 9 | 9 | 3 |
| | pSAN169 | 16 | 10 | 9 | 3 |
| Lisianthus '13431' | pSAN167 | 16 | 10 | 9 | 2 |
| | pSAN168 | 16 | 6 | 5 | 4 |
| | pSAN284 | 16 | 5 | 4 | 2 |
| | pSAN285 | 16 | 4 | 4 | 4 |
| | pSAN319 | 40 | 23 | 23 | 10 |
| Lisianthus '13497-6' | pSAN319 | 49 | 23 | 23 | 13 |
| | pSAN321 | 24 | 11 | 11 | 6 |
| Geranium Designer Scarlet | pSAN147 | 2 | 2 | 2 | NA[a] |
| | pSAN148 | 1 | 1 | 0 | NA |
| | pSAN163 | 16 | 10 | 3 | NA |
| | pSAN164 | 23 | 20 | 5 | NA |
| | pSAN165 | 9 | 6 | 1 | NA |
| | pSAN166 | 18 | 11 | 6 | NA |
| | pSAN167 | 27 | 25 | 7 | NA |
| | pSAN168 | 17 | 11 | 1 | NA |
| | pSAN169 | 6 | 3 | 2 | NA |
| | pSAN282 | 9 | 7 | 2 | NA |
| | pSAN283 | 5 | 4 | 2 | NA |
| | pSAN284 | 8 | 5 | 1 | NA |
| | pSAN285 | 30 | 24 | 5 | NA |
| | pSAN318 | 27 | 19 | 9 | NA |
| | pSAN319 | 12 | 7 | 2 | NA |
| | pSAN320 | 13 | 8 | 2 | NA |
| | pSAN321 | 17 | 11 | 6 | NA |

[a]not applicable
[b]not tested

Anti-Botrytis leaf disk bioassays: Following the anti-bacterial bioassay, candidate transgenic lines of petunia, lisianthus and poinsettia were selected for further analysis using an in vitro anti-fungal bioassay (geraniums were not screened using this leaf disk assay because in vitro plant growth is too slow). Briefly, twelve leaf disks (8 mm in diameter) from each tissue culture-maintained transformed lines (and an untransformed control) were punched out with a cork borer and placed onto moistened Whatman 3M paper inside a sterile plastic bioassay dish. A freshly-prepared suspension of Botrytis spores ($10^3$ spores in 2.5 μl) was then pipetted onto the leaf disk surface. The humidity chamber was sealed and the leaf disks left at 20° C. to permit disease development. For the next 3–14 days (timeline is species-dependent), disease progression was monitored and recorded as percentage of leaf disks infected. Table 5 shows representative results obtained from this bioassay. As can be observed, a significant reduction in disease incidence was observed for transgenic petunia, poinsettia, and lisianthus lines expressing a variety of antimicrobial peptides. The level of Botrytis infection was often reduced as much as 3 to 4-fold for many of the transgenic lines. In the case of lisianthus, infection of some transgenic lines was reduced by an order of magnitude, or more. This assay did not appear to detect any significant differences between transgenic lines which secreted the peptide versus those lines which retained the peptide in their cytosol. The overall results from each crop are given in Table 4.

TABLE 5

Reduced incidence of disease in *Botrytis cinerea*-inoculated leaf disks from three distinct antimicrobial peptide-expressing plants for each gene construct

| Plant | Plasmid | Peptide | Disease Incidence[a] | | |
|---|---|---|---|---|---|
| Petunia | 143 | MSI-99 | 26 | 30 | 31 |
| | 144 | D5-C | 31 | 41 | 50 |
| | 146 | MagII* | 55 | 62 | 64 |
| | 147 | MSI-99* | 36 | 60 | 70 |
| | 148 | D5-C* | 52 | 70 | 75 |
| Poinsettia | 142 | MagII | 58 | 65 | 68 |
| | 143 | MSI-99 | 48 | 61 | 69 |
| | 144 | D5-C | 62 | 68 | 72 |

TABLE 5-continued

Reduced incidence of disease in *Botrytis cinerea*-inoculated leaf disks from three distinct antimicrobial peptide-expressing plants for each gene construct

| Plant | Plasmid | Peptide | Disease Incidence[a] | | |
|---|---|---|---|---|---|
|  | 146 | MagII* | 51 | 51 | 59 |
|  | 163 | MagII | 66 | 68 | 70 |
|  | 165 | D5-C | 42 | 60 | 67 |
|  | 167 | MagII* | 50 | 69 | 80 |
|  | 168 | MSI-99* | 31 | 40 | 52 |
|  | 169 | D5-C* | 30 | 38 | 70 |
|  | 319 | MagII*/PGL* | 42 | 48 | 65 |
|  | 321 | PGL*/magII* | 47 | 66 | 80 |
| Lisianthus | 165 | D5-C | 10 | 37 | 38 |
|  | 169 | D5-C* | 10 | 41 | 47 |
|  | 319 | MagII*/PGL* | 0 | 7 | 22 |

[a]percent leaf disks infected relative to an untransformed control assigned a value of 100
*secreted version of peptide

Example 5

Magainin and PGL Classes of Antimicrobial Peptides Confer Resistance to Powdery Mildew in Petunia Whole petunia plants were challenged with the obligate fungal pathogen powdery mildew (Oidium sp.). for this test, a freshly-prepared suspension of powdery mildew spores was pipetted onto the leaves of greenhouse grown petunias. Plants were maintained under conditions which favored dosease development and then ranked for their disease resistance properties. The incidence of infection (percent inoculated leaves infected) and disease severity (colony area) were recorded.

As can be observed in Table 6, a number of transgenic V26 lines exhibited a reduced incidence of disease. for example, three pSAN147-expressing lines, (147-6, 147-8, and 147-11) all exhibited a 3 to 4-fold reduction on disease incidence. these lines contained the gene for MSI-99 in the secreted form. A more dramatic reduction in disease severity was observed as colony size was reduced from 5 to 50-fold in the transgenic lines compared to the untransformed control. Taken together, both disease incidence and severity are reduced, sometimes quite dramatically, in the transgenic, antimicrobial peptide-expressing petunia lines.

TABLE 6

Enhanced resistance to infection by powdery mildew in antimicrobial peptide expressing petunias

| Petunia Line | Disease Incidence[a] | Disease Severity[a] |
|---|---|---|
| V26-Control | 100 | 100 |
| 144-1 | 15 | 2 |
| 146-13 | 46 | 11 |
| 147-6 | 33 | 19 |
| 147-8 | 38 | 7 |
| 147-11 | 26 | 2 |
| 148-3 | 39 | 18 |

[a]percent infection of inoculated sites relative to an untransformed control assigned a value of 100 [b] relative colony size (area) compared to an untransformed control assigned a value of 100%.

Example 6

Magainin and PGL Classes of Antimicrobial Peptides Confer Resistance to an Obligate Fungal Pathogen, Powdery Mildew, in Poinsettia Similar to petunia, whole poinsettia plants were screened for resistance to the poinsetta powdery mildew pathogen (Oidium sp.). Twenty-six transgenic Angelika lines expressing either a single antimicrobial peptide or the combination of magainin 2 and PGL were tested in two different experiments. In addition, nineteen transgenic Freedom lines expressing either a single antimicrobial peptide or the combination of Magainin 2 and PGL were tested in two different experiments.

In the first experiment, fifteen transgenic Angelika lines and a non-transgenic control were inoculated by placing them in close proximity to a heavily infected source plant. The inoculum source plants were removed after seven days. At 15 days, the mildew colonies were quantified on a specific leaf area using a dissecting microscope and lateral illumination of the leaves. The maximum number of conidia observed per catenulate chain was also recorded as a measure of colony age and productivity. Twenty days after initiation, the colonies were again quantified on a specific leaf area without the aid of magnification. At 22 days, the conidial crop from each plant line was harvested and quantified.

Colonies were plainly visible without magnification two weeks after initiation. The density of mildew colonies was significantly and substantially reduced from control levels on several transgenic lines; most notably 148-15 (D5-C*S), 168-7 (MSI-99*S), 146-6 (Mag 2*S), 167-2 (Mag 2*S), and 168-24 (MSI-99*S) (Table 7). The length of the latent period (generation time), as indirectly measured by conidia per chain, was significantly increased above control levels on all transgenic lines (Table 7). Resistance to powdery mildew continued to be expressed as reduced density of colonization when plants were again examined on day twenty (Table 8). The greatest reduction of disease was shown by lines 168-7 (MSI-99*S), 167-2 (Mag 2*S), and 146-6 (Mag 2*S).

TABLE 7

Severity of powdery mildew and conidial production on transgenic and control poinsettia 15 days after initiation.

| | Colonies per 6X field of view[x] | | | Conidia per chain | | |
|---|---|---|---|---|---|---|
| Line | Mean | SE | CV(%) | Mean | SE | CV(%) |
| Control | 30.6 | 5.52 | 18 | 4.6 | 0.67 | 15 |
| 320-6 | 21.3 | 6.48 | 30 | 1.8 | 0.49 | 27 |
| 148-15 | 3.7 | 1.41 | 38 | 1.6 | 0.79 | 49 |
| 165-7 | 14.7 | 4.99 | 34 | 2.2 | 0.76 | 35 |
| 320-5 | 8.7 | 1.58 | 18 | 2.6 | 0.52 | 20 |
| 168-7 | 6.3 | 2.93 | 47 | 1.4 | 0.67 | 48 |
| 146-6 | 6.0 | 3.41 | 57 | 2.0 | 0.72 | 36 |
| 167-3 | 4.1 | 1.70 | 41 | 2.2 | 0.96 | 44 |
| 162-4 | 9.0 | 3.42 | 38 | 2.2 | 0.49 | 22 |
| 167-2 | 6.6 | 2.24 | 34 | 1.8 | 0.65 | 36 |
| 169-40 | 13.0 | 4.72 | 36 | 2.8 | 0.49 | 18 |
| 168-24 | 5.3 | 3.40 | 64 | 2.0 | 0.83 | 41 |
| 320-7 | no data | | | | | |
| 163-11 | no data | | | | | |
| 143-6 | no data | | | | | |
| 169-33 | no data | | | | | |

[x]Mean of three 6X fields of view per leaf. SE = standard error of the mean. CV = coefficient of variation (ratio of standard error to mean expressed as %)

TABLE 8

Severity of powdery mildew on transgenic and
control Angelika poinsettia twenty days after initiation and
production of conidia twenty-two days after initiation.

| Line | Colonies per leaf segment[x] | | | Conidia per square centimeter* | | |
|---|---|---|---|---|---|---|
| | Mean | SE | CV(%) | Mean | SE | CV(%) |
| Control | 23.4 | 1.39 | 6 | 87.7 | 23.7 | 27 |
| 320-6 | 30.2 | 6.64 | 22 | 103.0 | 52.9 | 51 |
| 148-15 | 10.2 | 3.44 | 34 | 30.3 | 17.7 | 58 |
| 165-7 | 27.0 | 4.59 | 17 | 59.0 | 14.7 | 25 |
| 320-5 | 11.0 | 3.45 | 31 | 12.1 | 1.9 | 16 |
| 168-7 | 3.6 | 1.83 | 51 | 18.6 | 0.0 | 0 |
| 146-6 | 5.4 | 3.39 | 63 | 4.5 | 0.0 | 0 |
| 167-3 | 7.2 | 3.89 | 54 | 3.0 | 3.7 | 123 |
| 162-4 | 9.0 | 3.94 | 44 | 10.6 | 10.3 | 97 |
| 167-2 | 4.4 | 2.17 | 49 | 4.5 | 0.0 | 0 |
| 169-40 | 12.2 | 4.68 | 38 | 60.5 | 21.9 | 36 |
| 168-24 | 6.8 | 2.49 | 37 | 3.0 | 1.9 | 63 |
| 320-7 | 10.2 | 4.98 | 26 | 53.0 | 34.6 | 65 |
| 163-11 | 19.6 | 6.10 | 31 | 3.8 | 13.3 | 38 |
| 143-6 | 13.6 | 6.11 | 45 | 31.8 | 22.5 | 71 |
| 169-33 | 19.2 | 4.34 | 23 | 46.9 | 12.2 | 26 |

[x]Mean number of colonies per leaf segment defined by the midvein, two lateral veins, and the leaf margin. The number of colonies per segment was recorded on the top two fully expanded leaves on each of three plants per treatment. SE = standard error of the mean. CV = coefficient of varition (ratio of standard error to mean expressed as %).
*All infected leaves were removed from individual test plants and were beaten against the shroud of a rotary fan producing a wind speed of approximately 15 kph to dislodge conidia. An 18-mm square coverglass was placed 1 meter downwind to capture a sample of the total airborne spores from each plant. The coverglass was mounted in lactoglycerol and cotton-blue, examined at 160 X, and the number of conidida per 160 X transect was recorded. SE = standard error of the mean. CV = coefficient of varition (ratio of standard error to mean expressed as %).

The total biomass of sporulating mildew colonies was estimated by sampling airborne conidia downwind of whole plants. Very few conidia were trapped downwind of 146-6 (Mag 2*S), 167-3 (Mag 2*S), 167-2 (Mag 2*S), and 168-24 (MSI-99*S) (Table 8). Transgenic line 168-7 (MSI-99*S), which had the lowest number of mildew colonies on day 20, ranked seventh in reduction of sporulation (Table 8), although sporulation was still reduced by nearly 80% from the control.

In the second experiment, 12 transgenic Angelika lines and the non-transgenic control were inoculated as described above, except that the inoculum source plants were removed after only 24 hrs. Thirteen days after initiation, the number of colonies on the most severely infected leaf on each plant was recorded. Two transgenic lines, 319-10 (Mag 2*S/PGL combination) and 145-15 (MSI-55*S), displayed reduced density of mildew colonies that was significantly lower than the untransformed control (Table 9).

TABLE 9

Severity of powdery mildew on control and
transgenic lines of poinsettia 13 days after initiation

| Line error | Colonies per infected leaf[x] | |
|---|---|---|
| | Mean | Standard |
| Control | 31.8 | 9.76 |
| 319-1 | 53.5 | 20.28 |
| 319-3 | 35.3 | 13.54 |
| 148-5 | 27.8 | 12.95 |
| 318-3 | 85.3 | 49.45 |
| 319-4 | 21.3 | 7.73 |

TABLE 9-continued

Severity of powdery mildew on control and
transgenic lines of poinsettia 13 days after initiation

| Line error | Colonies per infected leaf[x] | |
|---|---|---|
| | Mean | Standard |
| 146-4 | 37.8 | 24.84 |
| 320-5 | 31.5 | 10.24 |
| 145-15 | 18.0 | 5.74 |
| 318-1 | 48.8 | 30.05 |
| 319-7 | 5.3 | 1.69 |
| 145-16 | 33.5 | 6.27 |
| 319-5 | 42.0 | 21.22 |

[x]The most severely infected leaf on each plant was selected, and the total number of colonies per leaf were recorded.

In two additional experiments, 19 transgenic Freedom lines and the untransformed control were inoculated by blowing conidiospores across the plants from heavily infected source plants. Plants were arranged in a randomized complete block design on a single greenhouse bench. Plants were rotated daily within each replicated block and the blocks were rotated daily on the bench. The number of mildew colonies on each plant was recorded in experiments three and four, seventeen and twenty-one days after inoculation. Of the nineteen transgenic lines evaluated in these experiment, three (168-38, 168-30, 168-14) bore significantly fewer colonies per plant than inoculated controls.

Overall, significant resistance to powdery mildew was expressed by 12 of the 26 transgenic Angelika lines tested and 3 of the 19 transgenic Freedom lines tested. The resistance was expressed as (i) a reduction in the number of colonies, (ii) an increase in the duration of the latent period, and (iii) a reduction in the number of airborne spores downwind of infected plants.

In view of the fact that all mildews on all crops have a similar infection process, the results presented herein suggest these antimicrobial peptides will be effective in essentially all crops against all other types of mildew.

Example 7

Antimicrobial Peptides Confer Resistance to an Obligate Fungal Pathogen, Rust, in Geranium Whole geranium plants were screened for resistance to the geranium rust pathogen, Puccinia pelargonii-zonalis. Fifteen transgenic lines of the cultivar Designer Scarlet expressing the various lytic peptide genes and gene combinations were tested in two experiments for resistance to the rust pathogen compared to the non-transgenic control. Briefly, plants were sprayed with a urediospore suspension and incubated under high humidity during the infection process. Three weeks after inoculation, the number of rust lesions per 10 leaves and the number of leaves infected per plant were recorded. Several transgenic lines tested expressed resistance to rust infection in that there was two to three fold reduction in the number of lesions/leaf compared to non-transgenic control lines.

Example 8

Magainin and PGL Classes of Antimicrobial
Peptides Confer Resistance to a Fungal Pathogen,
Phytophthora parasitica, in Petunia Twelve transgenic petunia V26 lines were screened for resistance to infection by Phytophthora parasitica. Plant lines were clonally propagated in the greenhouse and grown to multiple-branched plants approximately six inches tall. Ten zoospores of *P. parasitica* (raised in liquid culture) were inoculated onto two leaves on each of three stems per plant. After inoculation, plants were incubated in a moist chamber at 28° C. for 7 days and then the disease severity of each inoculated stem was recorded. The rating system used for disease severity is as follows: 0=healthy, 1=inoculated leaves browning, 2=inoculated leaves wilting, 3=stems infected and wilting, 4=stem collapsed.

The disease severity of the transgenic lines ranged from three transgenic lines that were not different from the control where the stems collapsed by 7 days, and five transgenic lines where only the inoculated leaf showed symptoms but the disease did not progress into the shoot. In the remaining four transgenic lines, the symptoms were delayed compared to the control line but eventually the inoculated shoots collapsed.

Many plants have diseases caused by Phytophthora sp. Other plant species transformed with genes for Magainin and PGL classes of peptides should also be resistant to Phytophthora.

Example 9

Antimicrobial Peptides Confer Resistance to Infection by *Botrytis cinerea* on Geranium Petals Transgenic antimicrobial peptide-expressing geraniums were acclimated to the greenhouse for two months. Florets of similar age were harvested from transgenic lines and the non-transformed control line, and the ends of the pedicels placed into microfuge tubes containing water. A spore suspension of *Botrytis cinerea* was prepared as described above and diluted to contain 50 spores/ml. Ten florets per transgenic line were sprayed with the spore suspension until droplets formed on the surface. The inoculated florets were incubated in a moist chamber at room temperature and the percent of flower petals infected per floret at 2, 3, and 4 days after inoculation and the percent of the petals that had greater than 50% of the area infected was recorded.

Of the 46 transgenic lines tested, thirteen showed a significant reduction in severity of Botrytis infection compared to the control (Table 10). A delay of infection in some of the transgenic lines meant that the florets senesced while Botrytis infection was still only pinpoint infections. The infection on florets from non-transgenic control plants usually involved >50% of each petal because the lesions had coalesced.

TABLE 10

*Botrytis cinerea* screen of detached florets from transgenic geranium lines

| Plasmid | Number of lines tested | Number of lines resistant |
| --- | --- | --- |
| pSAN147 | 2 | 0 |
| pSAN148 | 1 | 1 |
| pSAN163 | 1 | 0 |
| pSAN164 | 4 | 0 |
| pSAN165 | 1 | 0 |
| pSAN166 | 7 | 4 |
| pSAN167 | 8 | 1 |
| pSAN168 | 1 | 1 |
| pSAN169 | 4 | 0 |
| pSAN282 | 2 | 0 |
| pSAN283 | 1 | 0 |
| pSAN284 | 2 | 0 |
| pSAN285 | 5 | 3 |

TABLE 10-continued

*Botrytis cinerea* screen of detached florets from transgenic geranium lines

| Plasmid | Number of lines tested | Number of lines resistant |
| --- | --- | --- |
| pSAN318 | 6 | 3 |
| pSAN320 | 1 | 0 |

Example 10

Magainin and PGL Classes of Antimicrobial Peptides Confer Resistance to Infection by *Botrytis cinerea* on Poinsettia Shoots Transgenic poinsettia lines which were positive for antimicrobial peptide activity in both the in vitro anti-bacterial assay and anti-Botrytis leaf disk assays were advanced to the next stages of disease screening. A second anti-Botrytis assay was developed to assess disease resistance on inoculated poinsettia cuttings. Briefly, shoots were harvested from greenhouse-grown transgenic plants and disinfected in a solution of 10% Clorox for five minutes, rinsed in water and then dipped in a spore suspension ($5 \times 10^5$ spores/ml). Inoculated shoots were incubated in a plastic bag for 2 days and then placed into wet oasis plugs under mist bed conditions to simulate commercial rooting practices. The disease incidence (percentage of cuttings infected) was recorded regularly and compared to inoculated, untransformed control shoots.

As can be observed in Table 11, the untransformed control shoots were sensitive to infection by Botrytis and quickly became heavily infected (disease ratings of 3–4). In contrast, a number of the antimicrobial peptide-expressing lines showed greatly reduced symptoms after inoculation. Line 169-40, expressing D5-C*S, consistently showed disease ratings of ~1 or less in the three bioassays. Other transgenic lines which showed significantly reduced levels of Botrytis infection (all with a disease rating of ~≦2) included 163-11 (Mag 2), 167-3 (Mag 2*S), and 168-7 and 168-24 (MSI-99*S). These results strongly support the conclusion that significant levels of resistance to Botrytis infection on poinsettia shoots are conferred by the antimicrobial peptides.

TABLE 11

Disease severity of transgenic Algelika cuttings inoculated with *Botrytis cinerea*

| | Disease index[a] Experiment number | | |
| --- | --- | --- | --- |
| Line | 1 | 2 | 3 |
| Control | 2.4 | 3.4 | 3.6 |
| 143-6 | 1.8 | 1.0 | 3.6 |
| 146.6 | 3.0 | 0.8 | 1.2 |
| 148-15 | 1.4 | 1.2 | 2.6 |
| 162-4 | 2.4 | 0 | 1.4 |
| 163.11 | 2.2 | 1.2 | 1.6 |
| 165-7 | 2.2 | 0.8 | 1.6 |
| 167-2 | 3.4 | 2.2 | 3.0 |
| 167-3 | 2.2 | 0.8 | 1.4 |
| 168-7 | 1.6 | 1.6 | 2.0 |
| 168-24 | 1.8 | 2.6 | 2.0 |

TABLE 11-continued

Disease severity of transgenic Algelika cuttings inoculated with Botrytis cinerea

| | Disease index[a] Experiment number | | |
|---|---|---|---|
| Line | 1 | 2 | 3 |
| 169-33 | 2.2 | 0.6 | 2.2 |
| 169-40 | 1.4 | 0.2 | 1.2 |

[a]mean disease index for five infected cuttings where 0 = uninfected, 1 = one older leaf infected or light infection on the young leaves, 2 = young leaves falling off due to infection or servere infection on older leaves, 3 = all leaves infected but <50% of leaf area infected, 4 = all leaves severely infected and >50% of leaf area infected, 5 = shoot is collapsed Example 11

Magainin and PGL Classes of Antimicrobial Peptides Confer Resistance to Infection by Rhizoctonia solani on Poinsettia Shoots In addition to screening poinsettia cuttings for resistance to Botrytis cinerea, we also screened for resistance to the fungal pathogen Rhizoctonia solani. Fifteen shoots were harvested from greenhouse-grown stock plants of five transgenic lines and the non-transgenic control. Cuttings were inoculated by placing an agar plug cut from a 1 week old culture of the fungus into the hole in the oasis in which the poinsettia cuttings are typically rooted. Each cutting was pushed into the hole within the oasis that contained a plug of mycelium. Inoculated cuttings were arranged in 3 replicates of five cuttings and incubated in the greenhouse under mist. The number of cuttings that rotted due to infection was recorded daily.

As can be observed in Table 12, the disease incidence for the non-transformed control ranged from 50% to 67% in three separate experiments. One transgenic line, 168-7, expressing the gene for the antimicrobial peptide MSI-99 in the secreted form, demonstrated a consistant reduction in disease incidence compared to the control. This same transgenic line (168-7) also demonstrated resistance to Botrytis cinerea (see Table 11) as well as powdery mildew (see Tables 7 and 8).

TABLE 12

Disease incidence on transgenic poinsettia cv. Angelika cuttings inoculated with Rhizoctonia solani

| | Disease Incidence[a] Experiment No. | | |
|---|---|---|---|
| Plant line | 1 | 2 | 3 |
| Control | 67% | 67 | 50 |
| 162-4 | 87 | 60 | 70 |
| 165-7 | 67 | 40 | 50 |
| 167-24 | 93 | 53 | 30 |
| 168-7 | 13 | 13 | 33 |
| 169-40 | 93 | 47 | 60 |

[a]Disease incidence is the mean % of the cuttings that rotted at 10–13 days after inoculation Example 12

Magainin and PGL Classes of Antimicrobial Peptides Confer Resistance to Infection by Erwinia carotovora ss carotovora on Poinsettia Shoots To assess whether increased levels of resistance to infection by a bacterial pathogen had been conferred by the antimicrobial peptides, poinsettia shoots were inoculated with Erwinia carotovora ss carotovora. Twelve shoots from greenhouse-grown transgenic plants were trimmed to a length of three inches and all but three leaves were removed. A wound was made on the stem 1 inch from the stem tip with a sterile toothpick. The wound site was then inoculated with a pipette tip containing a 2 $\mu$l droplet of $1\times10^4$ colony forming units (cfu's) of logarithmic phase Erwinia carotovora. Inoculated shoots were stuck into wet oasis plugs and then incubated under mist in the greenhouse. The incidence of disease (number of rotted cuttings) was recorded daily for one week after inoculation.

All of the transgenic lines tested showed some degree of resistance to infection by Erwinia carotovora ss carotovora (see the Figure). In the experiment presented in the Figure, two transgenic lines 167-3 (Mag2*S) and 169-40 (D5-C*S), did not develop any sign of Erwinia soft rot. The other eight transgenic lines showed reduction in disease incidence through the course of the experiment and a delay in disease development. Two lines, 167-2 (Mag2*S) and 165-2 (D5-C), did not develop soft rot until five days after inoculation while the control line had 18% of the shoots infected on day 3 and 75% of the shoots infected by day 5.

Magainin and PGL classes of peptides confer resistance to the bacterial pathogen Ecc. Since the antimicrobial peptides are more active against prokaryotes than eukaryotes and we have demonstrated resistance to several fungal pathogens in several plant species, we would expect resistance to various bacterial pathogens in all plant species.

Example 13

Magainin and PGL Classes of Antimicrobial Peptides Confer Resistance to Infection by Botrytis cinerea on Petunia Petals in Field-Grown plants A field trial to evaluate transgenic petunia 'V26' for resistance to Botrytis cinerea infection was performed. Botrytis cinerea causes gray mold of petunia flowers under conditions of high humidity. Rooted cuttings of two transgenic lines expressing MSI-99 in either the non-secreted or secreted form were included in this trial. Each plant line was represented by four replicates of six plants per replicate. Petunias were spaced in double rows one foot apart with four feet between the double rows. Each plant line was represented in each of four rows of double plants. The order of plants within each double row was randomized.

The incidence (percent flowers infected) and severity of Botrytis infection was recorded weekly through the season. Ten flowers were randomly selected on each plant and the number of flowers infected was recorded as well as the severity of infection of each flower. Severity was rated as Class I (0–10% of the flower infected), Class II (11%–90% of the flower infected), Class III (>90% of the flower infected). The field was frequently irrigated overhead to encourage Botrytis infection. One of the lines, 147-8, which secreted the peptide into the extracellular space consistently exhibited few, if any, Class III flowers compared to the untransformed V26 line. Similarly, line 147-8 also showed reduced numbers of Class II flowers throughout much of the trial period. The other antimicrobial peptide-expressing line did not exhibit any obvious Botrytis resistance traits compared to the non-transformed control.

We have demonstrated resistance to Botrytis cinerea in geranium flowers (Example 9), poinsettia shoots (Example 10) and petunia flowers (Example 13) conferred by Magainin and PGL classes of antimicrobial peptides.

Consequently, similar resistance to *Botryis cinerea* would be expected to be observed in other plant species that express these peptides.

Example 14

The Effect of Antimicrobial Peptides on the Poinsettia Phytoplasma

Lee et al., *Nature Biotechnology* 15:178–182 (1997) recently demonstrated that the free-branching phenotype in commercial poinsettias is caused by the presence of a mycoplasma-like organism (MLO) or phytoplasma, as it has now been designated, within the phloem cells of the vascular system. Since MLO's are prokaryotic-like microorganisms, the potential for antimicrobial peptide-mediated killing of the phytoplasma existed. To examine this possibility, transgenic poinsettia lines were grafted onto commercial, branching Angelika rootstock. Grafting was required since tissue culture conditions eradicate the phytoplasma from the poinsettia tissue. Fifteen transgenic Angelika lines containing secreted or non-secreted single antimicrobial peptides, were grafted to determine whether the antimicrobial peptides affected the phytoplasma, and thus the branching habit. After a 68-day grafting period, cuttings of the transgenic (and non-transgenic control) lines were rooted, potted, grown for 3 weeks and pinched to 9 nodes. Six weeks after pinching, the length of the lateral branches at each node was measured.

As can be observed in Table 13, both branching and non-branching phenotypes were observed. Of the nine lines which were secreting the peptide into the extracellular space, only 2 of 9 (22%) were found to be non-branching. In contrast, 50% (3/6) of the lines which retain the peptide in their cytosol were observed to give a non-branching phenotype. Since the phytoplasma is thought to reside in the cytosol of the cell, the higher percentage of nonbranching phenotypes in the lines which accumulate the peptide in the cytosol is consistent with the idea that exposure of the phytoplasma to the antimicrobial peptides might have lethal consequences. Since the phytoplasma cannot be maintained outside the plant, no in vitro data existed a priori on the sensitivity of the phytoplasma to the peptides. However, these observations strongly suggest that expression of antimicrobial peptides in other plants might be an effective manner in which to control diseases which are caused by infectious MLO agents. It should be noted that a branching phenotype was observed in 100% of the poinsettia lines (not transformed with antimicrobial peptide genes) recovered after being subjected to the same transformation regime as the antimicrobial peptide-expressing lines. This strongly indicates that tissue culture conditions alone are not responsible for the non-branching phenotype observed in 33% (5/15) of the antimicrobial peptide-expressing lines examined.

TABLE 13

The effect of antimicrobial peptides on lateral shoot growth of transgenic poinsettias that were grafted to restore the branching habit

| Line Phenotype | Peptide | Avg. shoot length nodes 1–3 (cm) | nodes 4–9 (cm) | Branch Type |
|---|---|---|---|---|
| Nongrafted control 1 | NA[a] | 16.0 | 0.0 | NB[b] |
| Nongrafted control I | NA | 17.0 | 0.3 | NB |
| Grafted control | NA | 10.6 | 9.8 | B[c] |
| Commercial Angelika 1 | NA | 15.0 | 14.2 | B |
| Commercial Angelika 2 | NA | 10.6 | 9.5 | B |
| 162-4 | MSI-55 | 14.3 | 17.2 | B |
| 162-7 | MSI-55 | 21.3 | 0.0 | NB |
| 163-6 | Mag2 | 25.3 | 0.0 | NB |
| 163-11 | Mag2 | 12.6 | 0.2 | NB |
| 165-2 | D5-C | 12.0 | 11.8 | B |
| 165-7 | D5-C | 12.6 | 12.6 | B |
| 167-2 | Mag2*S | 8.6 | 11.2 | B |
| 167-3 | Mag2*S | 10.3 | 6.0 | B |
| 167-24 | Mag2*S | 12.6 | 13.3 | B |
| 168-7 | MSI-99*S | 9.3 | 5.0 | B |
| 168-22 | MSI-99*S | 16.3 | 0.1 | NB |
| 168-24 | MSI-99*S | 6.3 | 6.0 | B |
| 169-18 | MSI-99*S | 16.3 | 0.1 | B |
| 169-33 | D5-C*S | 20.0 | 0.8 | NB |
| 169-40 | D5-C*S | 13.6 | 11.8 | B |

[a]not applicable
[b]NB denotes non-branched
[c]B denotes branched

We have demonstrated Magainin and PGL classes of peptides confer resistance to four major fungal pathogens (powdery mildew, Botrytis, Rhizoctonia, and Phytophthora), one bacterial pathogen (Erwinia), and phytoplasma in three plant species (petunia, poinsettia, and geranium). In addition, we showed antimicrobial peptide activity in transgenic lisianthus. We also showed that the Magainin and PGL classes of antimicrobial peptides are active against the bacterium Pseudomonas and the fungal pathogens Fusarium and Thielaviopsis in vitro. We therefore expect that when the Magainin and PGL classes of peptides are produced in any plant species they will confer resistance to a wide range of fungal, bacterial, and/or phytoplasma pathogens.

We claim:

1. A method of conferring to a plant tissue resistance to one or more phytopathogens, the method comprising transforming the plant tissue with a nucleic acid coding for an antimicrobial peptide, wherein the nucleic acid comprises (a) SEQ ID NO: 5, SEQ ID NO: 9, or SEQ ID NO: 13, or (b) SEQ ID NO: 5, SEQ ID NO: 9, or SEQ ID NO: 13 having one or more degenerate nucleotide substitutions, provided at least 70% homology is retained.

2. A method of conferring to a plant tissue resistance to one or more phytopathogens, the method comprising transforming the plant tissue with a nucleic acid coding an antimicrobial peptide, wherein the nucleic acid comprises (a) SEQ ID NO: 7, SEQ ID NO: 11, SEQ ID NO: 15, or SEQ ID NO: 17, or (b) SEQ ID NO: 7, SEQ ID NO: 11, SEQ ID NO: 15, or SEQ ID NO: 17 having one or more degenerate nucleotide substitutions, provided at least 70% homology is retained.

3. A method of conferring to a plant tissue resistance to one or more phytopathogens, the method comprising transforming the plant tissue with a nucleic acid coding for an antimicrobial peptide, wherein the nucleic acid comprises SEQ ID NO: 5 or SEQ ID NO: 7 in combination with SEQ ID NO: 17, which combination nucleic acid, when expressed in a plant cell, expresses peptides SEQ ID NO: 6 or SEQ ID NO: 8 and SEQ ID NO: 18.

4. A method of conferring to a plant tissue resistance to one or more phytopathogens, the method comprising co-transforming the plant tissue with a nucleic acid comprising SEQ ID NO: 5 or SEQ ID NO: 7 and a nucleic acid comprising SEQ ID NO: 17.

5. The method according to one of claims 1–4, wherein the phytopathogen is bacterial or fungal.

6. The method according to one of claims 1–4, wherein the phytopathogen is phytoplasma.

7. The method according to one of claims 1–4, wherein the phytopathogen is powdery mildew.

8. The method according to claim 7, wherein the plant tissue is a poinsettia plant tissue.

9. The method according to claim 7, wherein the plant tissue is a petunia plant tissue.

10. The method according to one of claims 1–4, wherein the nucleic acid or nucleic acids further comprises a plant promotor.

11. The method according to claim 10, wherein the promoter is selected from E35S, UBQ3, and UBQ10.

12. A method of conferring to a plant tissue resistance to one or more phytopathogens, the method comprising transforming the plant tissue with a first and a second nucleic acid, wherein the first nucleic acid is (a) SEQ ID NO: 7, SEQ ID NO: 11, SEQ ID NO: 15, or SEQ ID NO: 17, or (b) SEQ ID NO: 7, SEQ D NO: 11, SEQ ID NO: 15, or SEQ ID NO: 17 having one or more degenerate nucleotide substitutions, provided at least 70% homology is retained, and the second nucleic acid is (i) SEQ ID NO: 5, SEQ ID NO: 9, or SEQ ID NO: 13, or (ii) SEQ ID NO: 5, SEQ ID NO: 9, or SEQ ID NO: 13 having one or more degenerate nucleotide substitutions, provided at least 70% homology is retained.

13. A plant tissue obtained by the method according to claim 1.

14. A plant tissue obtained by the method according to claim 2.

15. A plant tissue obtained by the method according to claim 3.

16. A plant tissue obtained by the method according to claim 4.

17. A plant tissue obtained by the method according to claim 5.

18. A plant tissue obtained by the method according to claim 6.

19. A plant tissue obtained by the method according to claim 7.

20. A plant tissue obtained by the method according to claim 8.

21. A plant tissue obtained by the method according to claim 9.

22. A plant tissue obtained by the method according to claim 10.

23. A plant tissue obtained by the method according to claim 11.

24. A plant tissue obtained by the method according to claim 12.

* * * * *

SEQUENCE LISTING

```
<160> NUMBER OF SEQ ID NOS: 18

<210> SEQ ID NO: 1
<211> LENGTH: 87
<212> TYPE: DNA
<213> ORGANISM: Artificial Sequence
<220> FEATURE:
<223> OTHER INFORMATION: Description of Artificial Sequence:  Gene
      encoding the cytosol localized antimicrobial peptide D5-C
```

```
<220> FEATURE:
<221> NAME/KEY: CDS
<222> LOCATION: (1)..(87)

<400> SEQUENCE: 1 atg aag agg aag cgt gca gtt aag agg gtg gga cgt cga ttg aag aag      48
Met Lys Arg Lys Arg Ala Val Lys Arg Val Gly Arg Arg Leu Lys Lys
 1               5                  10                  15 ctt gca aga aag atc gca agg ctc ggt gtg gct ttc taa                  87
Leu Ala Arg Lys Ile Ala Arg Leu Gly Val Ala Phe
             20                  25

<210> SEQ ID NO: 2
<211> LENGTH: 28
<212> TYPE: PRT
<213> ORGANISM: Artificial Sequence
<220> FEATURE:
<223> OTHER INFORMATION: Description of Artificial Sequence:  Amino
      acid sequence of the cytosol localized antimicrobial peptide D5-C

<400> SEQUENCE: 2

Met Lys Arg Lys Arg Ala Val Lys Arg Val Gly Arg Arg Leu Lys Lys
 1               5                  10                  15

Leu Ala Arg Lys Ile Ala Arg Leu Gly Val Ala Phe
             20                  25

<210> SEQ ID NO: 3
<211> LENGTH: 129
<212> TYPE: DNA
<213> ORGANISM: Artificial Sequence
<220> FEATURE:
<221> NAME/KEY: CDS
<222> LOCATION: (1)..(129)
<220> FEATURE:
<223> OTHER INFORMATION: Description of Artificial Sequence:  Coding
      sequence for the extracellular localized antimicrobial
      D5-C peptide

<400> SEQUENCE: 3 atg ctt ctc gct att gcc ttc ttg gca tca gtt tgc gtg tct tcc aag      48
Met Leu Leu Ala Ile Ala Phe Leu Ala Ser Val Cys Val Ser Ser Lys
 1               5                  10                  15 agg aag cgt gca gtt aag agg gtg gga cgt cga ttg aag aag ctt gca      96
Arg Lys Arg Ala Val Lys Arg Val Gly Arg Arg Leu Lys Lys Leu Ala
             20                  25                  30 aga aag atc gca agg ctc ggt gtg gct ttc taa                         129
Arg Lys Ile Ala Arg Leu Gly Val Ala Phe
         35                  40

<210> SEQ ID NO: 4
<211> LENGTH: 42
<212> TYPE: PRT
<213> ORGANISM: Artificial Sequence
<220> FEATURE:
<223> OTHER INFORMATION: Description of Artificial Sequence:  Amino
      acid sequence of the extracellular localized antimicrobial
      D5-C peptide

<400> SEQUENCE: 4

Met Leu Leu Ala Ile Ala Phe Leu Ala Ser Val Cys Val Ser Ser Lys
 1               5                  10                  15

Arg Lys Arg Ala Val Lys Arg Val Gly Arg Arg Leu Lys Lys Leu Ala
             20                  25                  30

Arg Lys Ile Ala Arg Leu Gly Val Ala Phe
         35                  40
```

<210> SEQ ID NO: 5
<211> LENGTH: 75
<212> TYPE: DNA
<213> ORGANISM: Artificial Sequence
<220> FEATURE:
<223> OTHER INFORMATION: Description of Artificial Sequence: Gene
    coding for the cytosolic localized antimicrobial magainin
    2 peptide
<220> FEATURE:
<221> NAME/KEY: CDS
<222> LOCATION: (1)..(75)

<400> SEQUENCE: 5

```
atg ggc atc gga aag ttc ctt cac agt gca aag aag ttc gga aag gcc      48
Met Gly Ile Gly Lys Phe Leu His Ser Ala Lys Lys Phe Gly Lys Ala
 1               5                  10                  15 ttc gtg ggt gag atc atg aac agt taa                                  75
Phe Val Gly Glu Ile Met Asn Ser
            20
```

<210> SEQ ID NO: 6
<211> LENGTH: 24
<212> TYPE: PRT
<213> ORGANISM: Artificial Sequence
<220> FEATURE:
<223> OTHER INFORMATION: Description of Artificial Sequence: Amino acid
    sequence of the cytosolic localized antimicrobial magainin
    2 peptide

<400> SEQUENCE: 6

```
Met Gly Ile Gly Lys Phe Leu His Ser Ala Lys Lys Phe Gly Lys Ala
 1               5                  10                  15

Phe Val Gly Glu Ile Met Asn Ser
            20
```

<210> SEQ ID NO: 7
<211> LENGTH: 120
<212> TYPE: DNA
<213> ORGANISM: Artificial Sequence
<220> FEATURE:
<223> OTHER INFORMATION: Description of Artificial Sequence: Gene
    coding for the extracellular localized antimicrobial magainin
    2 peptide
<220> FEATURE:
<221> NAME/KEY: CDS
<222> LOCATION: (1)..(120)

<400> SEQUENCE: 7

```
atg ctt ctc gct att gcc ttc ttg gca tca gtt tgc gtg tct tcc atg      48
Met Leu Leu Ala Ile Ala Phe Leu Ala Ser Val Cys Val Ser Ser Met
 1               5                  10                  15 ggc atc gga aag ttc ctt cac agt gca aag aag ttc gga aag gcc ttc      96
Gly Ile Gly Lys Phe Leu His Ser Ala Lys Lys Phe Gly Lys Ala Phe
            20                  25                  30 gtg ggt gag atc atg aac agt taa                                     120
Val Gly Glu Ile Met Asn Ser
        35
```

<210> SEQ ID NO: 8
<211> LENGTH: 39
<212> TYPE: PRT
<213> ORGANISM: Artificial Sequence
<220> FEATURE:
<223> OTHER INFORMATION: Description of Artificial Sequence: Amino
    acid sequence of the extracellular localized antimicrobial
    magainin 2 peptide

<400> SEQUENCE: 8

```
Met Leu Leu Ala Ile Ala Phe Leu Ala Ser Val Cys Val Ser Ser Met
 1               5                  10                  15

Gly Ile Gly Lys Phe Leu His Ser Ala Lys Lys Phe Gly Lys Ala Phe
            20                  25                  30

Val Gly Glu Ile Met Asn Ser
            35

<210> SEQ ID NO: 9
<211> LENGTH: 69
<212> TYPE: DNA
<213> ORGANISM: Artificial Sequence
<220> FEATURE:
<223> OTHER INFORMATION: Description of Artificial Sequence:  Gene
      coding for the cytosol localized antimicrobial MSI-55
      peptide
<220> FEATURE:
<221> NAME/KEY: CDS
<222> LOCATION: (1)..(69)

<400> SEQUENCE: 9 atg aag atc gcc gga aag ata gca aag att gcg ggg aaa atc gcg aag      48
Met Lys Ile Ala Gly Lys Ile Ala Lys Ile Ala Gly Lys Ile Ala Lys
 1               5                  10                  15 atc gct ggc aaa atc gcg taa                                          69
Ile Ala Gly Lys Ile Ala
            20

<210> SEQ ID NO: 10
<211> LENGTH: 22
<212> TYPE: PRT
<213> ORGANISM: Artificial Sequence
<220> FEATURE:
<223> OTHER INFORMATION: Description of Artificial Sequence:  Amino acid
      sequence of the cytosol localized antimicrobial MSI-55
      peptide

<400> SEQUENCE: 10

Met Lys Ile Ala Gly Lys Ile Ala Lys Ile Ala Gly Lys Ile Ala Lys
 1               5                  10                  15

Ile Ala Gly Lys Ile Ala
            20

<210> SEQ ID NO: 11
<211> LENGTH: 111
<212> TYPE: DNA
<213> ORGANISM: Artificial Sequence
<220> FEATURE:
<223> OTHER INFORMATION: Description of Artificial Sequence:  Gene
      coding for the extracellular localized antimicrobial
      MSI-55 peptide
<220> FEATURE:
<221> NAME/KEY: CDS
<222> LOCATION: (1)..(111)

<400> SEQUENCE: 11 atg ctt ctc gct att gcc ttc ttg gca tca gtt tgc gtg tct tcc aag      48
Met Leu Leu Ala Ile Ala Phe Leu Ala Ser Val Cys Val Ser Ser Lys
 1               5                  10                  15 atc gcc gga aag ata gca aag att gcg ggg aaa atc gcg aag atc gct      96
Ile Ala Gly Lys Ile Ala Lys Ile Ala Gly Lys Ile Ala Lys Ile Ala
            20                  25                  30 ggc aaa atc gcg taa                                                 111
Gly Lys Ile Ala
        35
```

```
<210> SEQ ID NO: 12
<211> LENGTH: 36
<212> TYPE: PRT
<213> ORGANISM: Artificial Sequence
<220> FEATURE:
<223> OTHER INFORMATION: Description of Artificial Sequence:  Amino acid
      sequence of the extracellular localized antimicrobial
      MSI-55 peptide

<400> SEQUENCE: 12

Met Leu Leu Ala Ile Ala Phe Leu Ala Ser Val Cys Val Ser Ser Lys
 1               5                  10                  15

Ile Ala Gly Lys Ile Ala Lys Ile Ala Gly Lys Ile Ala Lys Ile Ala
                20                  25                  30

Gly Lys Ile Ala
        35

<210> SEQ ID NO: 13
<211> LENGTH: 72
<212> TYPE: DNA
<213> ORGANISM: Artificial Sequence
<220> FEATURE:
<223> OTHER INFORMATION: Description of Artificial Sequence:  Gene
      coding for the cytosol localized antimicrobial MSI-99
      peptide
<220> FEATURE:
<221> NAME/KEY: CDS
<222> LOCATION: (1)..(72)

<400> SEQUENCE: 13 atg gga atc ggc aag ttc ctc aag agc gca aag aag ttt ggc aag gcc      48
Met Gly Ile Gly Lys Phe Leu Lys Ser Ala Lys Lys Phe Gly Lys Ala
 1               5                  10                  15 ttc gtg aag atc ctg aac tcc taa                                      72
Phe Val Lys Ile Leu Asn Ser
            20

<210> SEQ ID NO: 14
<211> LENGTH: 23
<212> TYPE: PRT
<213> ORGANISM: Artificial Sequence
<220> FEATURE:
<223> OTHER INFORMATION: Description of Artificial Sequence:  Amino acid
      sequence of the cytosol localized antimicrobial MSI-99
      peptide

<400> SEQUENCE: 14

Met Gly Ile Gly Lys Phe Leu Lys Ser Ala Lys Lys Phe Gly Lys Ala
 1               5                  10                  15

Phe Val Lys Ile Leu Asn Ser
            20

<210> SEQ ID NO: 15
<211> LENGTH: 117
<212> TYPE: DNA
<213> ORGANISM: Artificial Sequence
<220> FEATURE:
<223> OTHER INFORMATION: Description of Artificial Sequence:  Gene
      coding for the extracellular localized antimicrobial
      MSI-99 peptide
<220> FEATURE:
<221> NAME/KEY: CDS
<222> LOCATION: (1)..(117)

<400> SEQUENCE: 15 atg ctt ctc gct att gcc ttc ttg gca tca gtt tgc gtg tct tcc atg      48
Met Leu Leu Ala Ile Ala Phe Leu Ala Ser Val Cys Val Ser Ser Met
 1               5                  10                  15
```

```
gga atc ggc aag ttc ctc aag agc gca aag aag ttt ggc aag gcc ttc      96
Gly Ile Gly Lys Phe Leu Lys Ser Ala Lys Lys Phe Gly Lys Ala Phe
            20                  25                  30 gtg aag atc ctg aac tcc taa                                         117
Val Lys Ile Leu Asn Ser
        35
```

<210> SEQ ID NO: 16
<211> LENGTH: 38
<212> TYPE: PRT
<213> ORGANISM: Artificial Sequence
<220> FEATURE:
<223> OTHER INFORMATION: Description of Artificial Sequence: Amino acid
    sequence of the extracellular localized antimicrobial
    MSI-99 peptide

<400> SEQUENCE: 16

```
Met Leu Leu Ala Ile Ala Phe Leu Ala Ser Val Cys Val Ser Ser Met
 1               5                  10                  15

Gly Ile Gly Lys Phe Leu Lys Ser Ala Lys Lys Phe Gly Lys Ala Phe
            20                  25                  30

Val Lys Ile Leu Asn Ser
        35
```

<210> SEQ ID NO: 17
<211> LENGTH: 111
<212> TYPE: DNA
<213> ORGANISM: Artificial Sequence
<220> FEATURE:
<223> OTHER INFORMATION: Description of Artificial Sequence: Gene
    coding for the extracellular localized antimicrobial PGL
    peptide
<220> FEATURE:
<221> NAME/KEY: CDS
<222> LOCATION: (1)..(111)

<400> SEQUENCE: 17

```
atg ctt ctc gct att gcc ttc ttg gca tca gtt tgc gtg tct tcc gga      48
Met Leu Leu Ala Ile Ala Phe Leu Ala Ser Val Cys Val Ser Ser Gly
 1               5                  10                  15 atg gcc tct aag gca ggt gct atc gcc ggc aaa atc gcg aag gtg gca      96
Met Ala Ser Lys Ala Gly Ala Ile Ala Gly Lys Ile Ala Lys Val Ala
            20                  25                  30 ttg aag gcc ctt taa                                                 111
Leu Lys Ala Leu
        35
```

<210> SEQ ID NO: 18
<211> LENGTH: 36
<212> TYPE: PRT
<213> ORGANISM: Artificial Sequence
<220> FEATURE:
<223> OTHER INFORMATION: Description of Artificial Sequence: Amino acid
    sequence of the extracellular localized antimicrobial PGL peptide

<400> SEQUENCE: 18

```
Met Leu Leu Ala Ile Ala Phe Leu Ala Ser Val Cys Val Ser Ser Gly
 1               5                  10                  15

Met Ala Ser Lys Ala Gly Ala Ile Ala Gly Lys Ile Ala Lys Val Ala
            20                  25                  30

Leu Lys Ala Leu
        35
```